United States Patent [19]
Heiligenstein

[11] Patent Number: 6,028,070
[45] Date of Patent: Feb. 22, 2000

[54] TREATMENT OF OPPOSITIONAL DEFIANT DISORDER

[75] Inventor: John Harrison Heiligenstein, Indianapolis, Ind.

[73] Assignee: Eli Lilly and Company, Indianapolis, Ind.

[21] Appl. No.: 09/156,289

[22] Filed: Sep. 17, 1998

Related U.S. Application Data

[60] Provisional application No. 60/059,629, Sep. 23, 1997.

[51] Int. Cl.[7] .................... A61K 31/535; A61K 31/38; A61K 31/165; A61K 31/135
[52] U.S. Cl. ..................... 514/238.8; 514/239.2; 514/239.5; 514/438; 514/620; 514/649; 514/651; 514/653
[58] Field of Search ............... 514/238.8, 239.2, 514/239.5, 438, 620, 649, 651, 653

[56] References Cited

U.S. PATENT DOCUMENTS

| | | | |
|---|---|---|---|
| 4,229,449 | 10/1980 | Melloni et al. | 514/239.2 |
| 5,532,268 | 7/1996 | Wong et al. | 514/432 |
| 5,658,590 | 8/1997 | Heiligenstein et al. | 424/464 |
| 5,696,168 | 12/1997 | Heiligenstein et al. | 514/649 |

FOREIGN PATENT DOCUMENTS

| | | |
|---|---|---|
| 0 687 472 | 12/1995 | European Pat. Off. . |
| WO 96 12485 | 5/1996 | WIPO . |

OTHER PUBLICATIONS

Chemical Abstract 89:157222, "Comparison of Inhibition of Monoamine Uptake by Cocaine, Methylphenidate, and Amphetamine", 1978.

*Journal of Abnormal Child Psychology.* Barkley, R.A. et al., Adolescents with attention deficit hyperactivity disorder: mother–adolescent interactions, family beliefs and conflicts, and maternal psychopathology Abstract, Jun. 1992, vol. 20, No. 3, pp. 263–288.

Diagnostic and Statistical Manual of Developmental Disorders, Fourth Edition (DSM–IV)pp. 78–94.

POPPER, C.W.: "Antidepressants in the treatment of attention–deficit/hyperactivity disorder" *The Journal of Clinical Psychiatry*, vol. 58, no. suppl. 13, 1997, pp. 14–29.

Greydanus, D. E. et al.: "The rebellious adolescent: Evaluation and management of oppositional and conduct disorders" *Pediatric Clinics of North America*, vol. 44, no. 6, pp. 1457–1485.

*Primary Examiner*—Frederick Krass
*Attorney, Agent, or Firm*—Robert D. Titus

[57] ABSTRACT

Norepinephrine reuptake inhibitors are used to treat oppositional defiant disorder.

6 Claims, No Drawings

TREATMENT OF OPPOSITIONAL DEFIANT DISORDER

PRIORITY INFORMATION

This application claims the benefit of priority of U.S. Provisional Patent Application 60/059,629 filed Sep. 23, 1997.

FIELD OF THE INVENTION

The invention belongs to the fields of pharmaceutical chemistry and psychiatric medicine, and provides a method of treatment of the psychiatric disorder known as oppositional defiant disorder.

BACKGROUND OF THE INVENTION

Children and adolescents suffering from oppositional defiant disorder exhibit a pattern of hostile, defiant, and negative behavior more often than is commonly observed in other individuals of the same mental age. They are argumentative with adults, are often angry and resentful, frequently lose their temper, swear, defy rules and requests from adults, and deliberately engage in annoying behavior. They also tend to not see themselves as a problem, but rather justify their behavior as a response to unreasonable circumstances.

Oppositional defiant disorder (ODD) is many times treated with the same therapies employed for the treatment of Attention-deficit Hyperactivity Disorder (ADHD), e.g., methylphenidate (Ritalin™), which exhibits noradrenergic and dopaminergic effects. Gross has demonstrated that certain ODD symptoms may be ameliorated by augmentation of standard ADHD therapies with buspirone in certain patients (Gross, *J. Am. Acad. Child Adolesc. Psychiatry*, 34(10), 1260 (1995)). Many patients are refractory to these treatments, or discontinue treatment due to intolerable side effects. Furthermore, due to the high potential for substance abuse in oppositional defiant disorder patients, the use of stimulants such as methylphenidate is problematic.

The need for a safe and effective treatment for oppositional defiant disorder, without the disadvantages of current therapies, continues to be a concern of the psychiatric community.

SUMMARY OF THE INVENTION

The present invention provides a method of treating oppositional defiant disorder comprising the administration to a patient in need of such treatment of an effective amount of a norepinephrine reuptake inhibitor.

DETAILED DESCRIPTION

Many compounds, including those discussed at length below, are norepinephrine reuptake inhibitors, and no doubt many more will be identified in the future. In the practice of the present invention, it is intended to include reuptake inhibitors which show 50% effective concentrations of about 1000 nM or less, in the protocol described by Wong et al., *Drug Development Research*, 6, 397 (1985). The norepinephrine reuptake inhibitors useful for the method of the present invention are characterized in being selective for the inhibition of neurotransmitter reuptake relative to their ability to act as direct agonists or antagonists at other receptors. Norepinephrine reuptake inhibitors useful for the method of the present invention include, but are not limited to:

Tomoxetine, (R)-(−)-N-methyl-3-(2-methylphenoxy)-3-phenylpropylamine, is usually administered as the hydrochloride salt. Tomoxetine was first disclosed in U.S. Pat. No. 4,314,081. The word "tomoxetine" will be used here to refer to any acid addition salt or the free base of the molecule. See, for example, Gehlert, et al., *Neuroscience Letters*, 157, 203–206 (1993), for a discussion of tomoxetine's activity as a norepinephrine reuptake inhibitor;

The compounds of formula I:

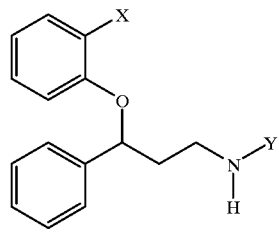

I wherein X is $C_1$–$C_4$ alkylthio, and Y is $C_1$–$C_2$ alkyl or a pharmaceutically acceptable salt thereof. The compounds of formula I were described in U.S. Pat. No. 5,281,624, of Gehlert, Robertson, and Wong, and in Gehlert, et al., *Life Sciences*, 55(22), 1915–1920, (1995). The compounds are there taught to be inhibitors of norepinephrine reuptake in the brain. It is also explained that the compounds exist as stereoisomers, and that they accordingly include not only the racemates, but also the isolated individual isomers as well as mixtures of the individual isomers. For example, the compounds of formula I include the following exemplary species:

N-ethyl-3-phenyl-3-(2-methylthiophenoxy)propylamine benzoate;

(R)-N-methyl-3-phenyl-3-(2-propylthiophenoxy) propylamine hydrochloride;

(S)-N-ethyl-3-phenyl-3-(2-butylthiophenoxy) propylamine;

N-methyl-3-phenyl-3-(2-ethylthiophenoxy)propylamine malonate;

(S)-N-methyl-3-phenyl-3-(2-tert-butylthiophenoxy) propylamine naphthalene-2-sulfonate;

(R)-N-methyl-3-(2-methylthiophenoxy)-3-phenylpropylamine;

Reboxetine (Edronax™), 2-[α-(2-ethoxy) phenoxybenzyl]morpholine, is usually administered as the racemate. It was first taught by U.S. Pat. No. 4,229,449, which describes its utility for the treatment of depression. Reboxetine is a selective norepinephrine reuptake inhibitor. The term "reboxetine" will be used here to refer to any acid addition salt or the free base of the molecule existing as the racemate or either enantiomer;

Duloxetine, N-methyl-3-(1-naphthalenyloxy)-3-(2-thienyl)propanamine, is usually administered as the hydrochloride salt and as the (+) enantiomer. It was first taught by U.S. Pat. No. 4,956,388, which shows its high potency. The word "duloxetine" will be used here to refer to any acid addition salt or the free base of the molecule;

Venlafaxine is known in the literature, and its method of synthesis and its activity as an inhibitor of serotonin and norepinephrine uptake are taught by U.S. Pat. No. 4,761,501. Venlafaxine is identified as compound A in that patent; and Milnacipran (N,N-diethyl-2-aminomethyl-1-phenylcyclopropanecarboxamide) is taught by U.S.

Pat. No. 4,478,836, which prepared milnacipran as its Example 4. The patent describes its compounds as antidepressants. Moret et al., *Neuropharmacology* 24, 1211–19 (1985), describe its pharmacological activities as an inhibitor of serotonin and norepinephrine reuptake.

All of the U.S. patents which have been mentioned above in connection with compounds used in the present invention are incorporated herein by reference.

A preferred duloxetine enteric formulation is a pellet formulation comprising a) a core consisting of duloxetine and a pharmaceutically acceptable excipient; b) an optional separating layer; c) an enteric layer comprising hydroxypropylmethylcellulose acetate succinate (HPMCAS) and a pharmaceutically acceptable excipient; d) an optional finishing layer. The following example demonstrates the preparation of a preferred such formulation.

EXAMPLE 10 mg Duloxetine Base/Capsule

| Bill of Materials | | |
|---|---|---|
| Beads | | |
| Sucrose - starch nonpareils, 20–25 mesh | 60.28 | mg |
| Duloxetine layer | | |
| Duloxetine | 11.21 | |
| Hydroxypropylmethylcellulose | 3.74 | |
| Separating layer | | |
| Hydroxypropylmethylcellulose | 2.51 | |
| Sucrose | 5.00 | |
| Talc, 500 mesh | 10.03 | |
| Enteric layer | | |
| HPMCAS, LF grade, Shin-Etsu Chemical Co., Tokyo, Japan | 25.02 | |
| Triethyl citrate | 5.00 | |
| Talc, 500 mesh | 7.52 | |
| Finishing layer | | |
| Hydroxypropylmethylcellulose | 8.44 | |
| Titanium dioxide | 2.81 | |
| Talc | Trace | |
| | 154.60 | mg |

The duloxetine layer was built up by suspending duloxetine in a 4% w/w solution of the hydroxypropylmethylcellulose in water, and milling the suspension with a CoBall Mill (Fryma Mashinen A G, Rheinfelden, Switzerland) model MS-12. A fluid bed dryer with a Wurster column was used to make this product, at a batch size of 1.0 kg. The separating layer was added from a 4% w/w solution of the hydroxypropyl-methylcellulose in water, in which the sucrose was also dissolved.

In order to prepare the enteric coating suspension, purified water was cooled to 10° C. and the polysorbate, triethyl citrate and silicone emulsion were added and dispersed or dissolved. Then the HPMCAS and talc were added and agitated until homogeneity was obtained, and the HPMCAS was fully neutralized by addition of ammonium hydroxide until solution of the polymer was complete. To this suspension, a carboxymethylcellulose aqueous solution, 0.5% w/w, was added and blended thoroughly. The enteric suspension was maintained at 20° C. during the coating process. The enteric suspension was then added to the partially completed pellets in the Wurster column at a spray rate of about 15 ml/min, holding the temperature of the inlet air at about 50° C. The product was dried in the Wurster at 50° C. when the enteric suspension had been fully added, and then dried on trays for 3 hours in a dry house at 60° C. A finishing layer was then applied which consisted of a 4.5% w/w/hydroxypropylmethyl-cellulose solution containing titanium dioxide and propylene glycol as plasticizer. The pellets were completely dried in the fluid bed dryer and then were then filled in size 3 gelatin capsules.

While all compounds exhibiting norepinephrine reuptake inhibition are useful for the method of the present invention, certain are preferred. It is preferred that the norepinephrine reuptake inhibitor is selective for norepinephrine over other neurotransmitters. It is also preferred that the norepinephrine reuptake inhibitor is selected from tomoxetine, reboxetine, or a compound of formula I. It is especially preferred that the norepinephrine reuptake inhibitor be selected from tomoxetine, reboxetine, or (R)-N-methyl-3-(2-methylthiophenoxy)-3-phenylpropylamine.

It will be understood by the skilled reader that most or all of the compounds used in the present invention are capable of forming salts, and that the salt forms of pharmaceuticals are commonly used, often because they are more readily crystallized and purified than are the free bases. In all cases, the use of the pharmaceuticals described above as salts is contemplated in the description herein, and often is preferred, and the pharmaceutically acceptable salts of all of the compounds are included in the names of them.

Many of the compounds used in this invention are amines, and accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, b-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid.

Administration

The dosages of the drugs used in the present invention must, in the final analysis, be set by the physician in charge of the case, using knowledge of the drugs, the properties of the drugs in combination as determined in clinical trials, and the characteristics of the patient, including diseases other than that for which the physician is treating the patient.

General outlines of the dosages, and some preferred dosages, can and will be provided here.

Tomoxetine: from about 5 mg/day to about 100 mg/day; preferably in the range from about 5 to about 70 mg/day; more preferably from about 10 to about 60 mg/day; and still more preferably from about 10 to about 50 mg/day;

Compounds of formula I: from about 0.01 mg/kg to about 20 mg/kg; preferred daily doses will be from about 0.05 mg/kg to 10 mg/kg; ideally from about 0.1 mg/kg to about 5 mg/kg;

Reboxetine: from about 1 to about 30 mg, once to four times/day; preferred, from about 5 to about 30 mg once/day;

Duloxetine: from about 1 to about 30 mg once/day; preferred, from about 5 to about 20 mg once/day;

Venlafaxine: from about 10 to about 150 mg once-thrice/day; preferred, from about 25 to about 125 mg thrice/day; and Milnacipran: from about 10 to about 100 mg once-twice/day; preferred, from about 25 to about 50 mg twice/day.

All of the compounds concerned are orally available and are normally administered orally, and so oral administration is preferred. However, oral administration is not the only route or even the only preferred route. For example, transdermal administration may be very desirable for patients who are forgetful or petulant about taking oral medicine. The drugs may also be administered by the percutaneous, intravenous, intramuscular, intranasal or intrarectal route, in particular circumstances. The route of administration may be varied in any way, limited by the physical properties of the drugs and the convenience of the patient and the caregiver.

The best description of oppositional defiant disorder is the diagnostic criteria published by the American Psychiatric Association in the DSM-III-R (Diagnostic and Statistical Manual of Mental Disorders, Third Edition-Revised (1987)), as follows.

Diagnostic Criteria for Oppositional Defiant Disorder

A. A disturbance of at least six months, during which at least five of the following are present:

(1) often loses temper (2) often argues with adults (3) often actively defies of refuses adult requests or rules, e.g., refuses to do chores at home (4) often deliberately does things that annoy other people, e.g., grabs other children's hats (5) often blames others for his or her own mistake (6) is often touchy or easily annoyed by others (7) is often angry and resentful (8) is often spiteful or vindictive (9) often swears or uses obscene language B. Does not meet the criteria for Conduct Disorder, and does not occur exclusively during the course of a psychotic disorder, Dysthymia, or a Major Depressive, Hypomanic, or Manic Episode.

Patients suffering from Oppositional Defiant Disorder also commonly suffer concomitantly from Attention-deficit Hyperactivity Disorder. The patient will benefit from the use of norepinephrine reuptake inhibitors in the amelioration of the symptoms of Oppositional Defiant Disorder regardless of this or other co-morbid conditions. Furthermore, a patient suffering from Oppositional Defiant Disorder and Attention-deficit Hyperactivity Disorder will receive benefit in the amelioration of symptoms of both conditions through the method of the present invention.

The method of the present invention is effective in the treatment of patients who are children or adolescents, and there is no significant difference in the symptoms or the details of the manner of treatment among patients of different ages. In general terms, however, for purposes of the present invention, a child is considered to be a patient below the age of puberty, and an adolescent is considered to be a patient from the age of puberty up to about 18 years of age.

Inhibition or Norepinephrine Reuptake

The ability of compounds to inhibit the reuptake of norepinephrine may be measured by the general procedure of Wong, et al., supra.

Male Sprague-Dawley rats weighing 150–250 gm are decapitated and brains are immediately removed. Cerebral cortices are homogenized in 9 volumes of a medium containing 0.32 M sucrose and 10 mM glucose. Crude synaptosomal preparations are isolated after differential centrifugation at 1000×g for 10 minutes and 17,000×g for 28 minutes. The final pellets are suspended in the same medium and kept in ice until use within the same day.

Synaptosomal uptake of $^3$H-norepinephrine is determined as follows. Cortical synaptosomes (equivalent to 1 mg of protein) are incubated at 37° C. for 5 minutes in 1 mL Krebs-bicarbonate medium containing also 10 mM glucose, 0.1 mM iproniazide, 1 mM ascorbic acid, 0.17 mM EDTA and 50 nM $^3$H-norepinephrine. The reaction mixture is immediately diluted with 2 mL of ice-chilled Krebs-bicarbonate buffer and filtered under vacuum with a cell harvester (Brandel, Gaithersburg, Md.). Filters are rinsed twice with approximately 5 mL of ice-chilled 0.9% saline and the uptake of $^3$H-norepinephrine assessed by liquid scintillation counting. Accumulation of $^3$H-norepinephrine at 4° C. is considered to be background and is subtracted from all measurements. The concentration of the test compound required to inhibit 50% of the $^3$H-norepinephrine accumulation ($IC_{50}$ values) are determined by linear regression analysis.

We claim:

1. A method of treating oppositional defiant disorder comprising administration to a patient in need of such treatment an effective amount of a norepinephrine reuptake inhibitor selective for norepinephrine over other neurotransmitters.

2. A method of claim 1 wherein the norepinephrine reuptake inhibitor is selected from the group consisting of tomoxetine, reboxetine and a compound of formula I:

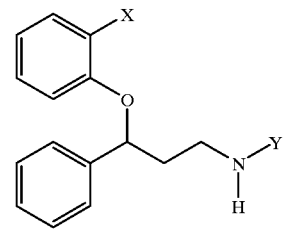

wherein X is $C_1$–$C_4$ alkylthio, and Y is $C_1$–$C_2$ alkyl or a pharmaceutically acceptable salt thereof.

3. A method of claim 2 wherein the norepinephrine reuptake inhibitor is tomoxetine.

4. A method of claim 2 wherein the norepinephrine reuptake inhibitor is tomoxetine hydrochloride.

5. A method of claim 2 wherein the norepinephrine reuptake inhibitor is reboxetine.

6. A method of claim 2 wherein the norepinephrine reuptake inhibitor is (R)-N-methyl-3-(2-methylthiophenoxy)-3-phenylpropylamine.

* * * * *